United States Patent [19]

Ginnaga et al.

[11] Patent Number: 4,885,359

[45] Date of Patent: Dec. 5, 1989

[54] METHOD FOR THE PURIFICATION OF LPF-HA

[75] Inventors: Akihiro Ginnaga; Tsukasa Nishihara; Tetsuo Kawahara; Sadao Susumi; Hiroshi Mizokami; Mitsuo Sakoh, all of Kumamoto, Japan

[73] Assignee: Juridical Foundation The Chemo-Sero-Therapeutic Research Institute, Kumamoto, Japan

[21] Appl. No.: 122,576

[22] Filed: Nov. 16, 1987

Related U.S. Application Data

[63] Continuation of Ser. No. 753,867, Jul. 11, 1985, abandoned.

[30] Foreign Application Priority Data

| | | | |
|---|---|---|---|
| Jul. 19, 1984 | [JP] | Japan | 59-150945 |
| Aug. 22, 1984 | [JP] | Japan | 59-175710 |
| Sep. 10, 1984 | [JP] | Japan | 59-190244 |

[51] Int. Cl.[4] ...................... C07K 15/04; C07K 17/12; A61K 37/02; A61K 39/10

[52] U.S. Cl. .................................... 530/396; 530/413; 530/825; 514/2; 424/88; 424/92; 424/95; 435/71.3; 435/803

[58] Field of Search ................. 424/92, 95, 88; 514/2; 435/803, 68; 530/396, 825, 413; 436/827

[56] References Cited

U.S. PATENT DOCUMENTS

| | | | |
|---|---|---|---|
| 3,184,394 | 5/1965 | Schmidtberger et al. | 424/92 |
| 4,022,758 | 5/1977 | Andersson et al. | 530/413 |
| 4,247,452 | 1/1981 | Irons et al. | 424/92 |
| 4,515,714 | 5/1985 | Kawahara et al. | 424/89 |
| 4,563,303 | 1/1986 | Ginnaga et al. | 435/68 |
| 4,687,738 | 8/1987 | Ginnaga et al. | 435/68 |
| 4,704,274 | 11/1987 | Sakuma et al. | 424/88 |

*Primary Examiner*—Jacqueline M. Stone
*Attorney, Agent, or Firm*—Wegner & Bretschneider

[57] ABSTRACT

Improved method for the purification of LPF-HA (Leucocytosis promoting factor hemagglutinin) on industrial scale which comprises contacting a LPF-HA-containing solution from culture media of *Bordetella pertussis* with a cellulose sulfate gel, a crosslinked polysaccharide sulfate gel, or a polysaccharide gel chemically bound with dextran sulfate, thereby adsorbing LPF-HA on the gel, and then eluting LPF-HA from the gel. Said method can give a highly purified LPF-HA which does not contain any other proteins, lipid, saccharides, etc. and further undesirable endotoxin, and hence can be used for producing various reagents, medicines and pertussis vaccine.

7 Claims, 1 Drawing Sheet

METHOD FOR THE PURIFICATION OF LPF-HA

This is a continuation of Ser. No. 753,867, filed 7/11/85, now abandoned.

The present invention relates to a method for the purification of LPF-HA (Leucocytosis-promoting Factor Hemagglutinin). More paticularly, it relates to a method for producing LPF-HA in a high yield and high purity by contacting an LPF-HA-containing solution obtained from culture media of *Bordetella pertussis* with a cellulose sulfate gel, a crosslinked polysaccharide sulfate gel, or a polysaccharide gel chemically bound with dextran sulfate, thereby adsorbing LPF-HA on the gel, and then eluting LPF-HA from the gel.

TECHNICAL FIELD

LPF-HA is an active substance produced by *B. pertussis* phase I and phase II strains which is not produced by *B. pertussis* phase III strain having no virulence or *Bordetella parapertussis, Bordetella bronchiseptica.* The LPF-HA is also called as *B. pertussis* toxin and is a protein having various physiological activities. The main physiological activities are a leucocytosis-promoting activity, an insulin secretion-enhancing activity, a histamine-sensitizing activity, a hemagglutinating activity, and the like. Particularly, because of the insulin secretion-enhancing activity, it is noticed that the LPF-HA may be useful for the treatment of diabetes.

Separately from the above physiological activities, it has recently been noticed that LPF-HA shows an important function in the prophylaxis of infection of *B. pertussis* and infectious disease thereof and hence is useful as an antigen for prophylaxis of infection of *B. pertussis* [cf. Pittman, M.; Review of Infectious Diseases, 1, 401–409 (1979), and Sato, Y. et al.; Seminars in Infectious Deiseases IV, Bacterial Vaccine, 380–385 (1982)].

Thus, it has been desired to develop an improved method for the separation and purification of LPF-HA simply and in a large quantity, for the purpose of studying the physiological activities of LPF-HA, of producing a medicine and of producing a pertussis vaccine having less side effect on industrial scale.

PRIOR ART

According to known methods, the separation and purification of LPF-HA is carried out by salting out a culture medium of *B. pertussis* with ammonium sulfate, extracting and dialyzing, and then subjecting the thus obtained material to ion exchange chromatography, gel filtration [cf. Arai, H.; Biochimica et Biophysica Acta, 444, 765 (1976)] or to sucrose concentration gradient centrifugation [cf. Sato, Y.; Infect. Immun., 6, 897–704 (1972)]. According to such known methods, however, it is difficult to obtain highly purified LPF-HA, and its yield is very low.

In order to obtain the desired highly pure LPF-HA in a comparatively large amount, it is also proposed that a supernatant of culture media of *B. pertussis* is passed through a column packed with hydroxyapatite to absorb LPF-HA thereon, followed by washing, eluting and then subjecting to affinity chromatography with concanavalin A-Sepharose (Con A-Sepharose, manufactured by Pharmacia) [cf. Yajima, M. et al.; J. Biochem., 83, 295–303 (1978)]. However, the affinity chromatography using concanavalin A as a ligand not only has an affinity with LPF-HA but also can adsorb saccharides, glycolipids and also other glycoproteins, and hence, it adsorbs other pertussis cell components such as F-HA (Filamentous Hemagglutinin) and cell membrane components, which results in difficulty of isolation of the desired highly pure LPF-HA. Thus, it is not suitable as an affinity chromatography for LPF-HA.

Since it has recently been found that human haptoglobin binds specifically to LPF-HA, it has been tried to purify LPF-HA by an affinity chromatography using as a ligand the human haptoglobin instead of the above concanavalin [cf. Iron, L. et al.; Biochimica et Biophysica Acta, 580, 175–185 (1979), and Cowell, J. et al.; Seminars in Infectious Diseases IV, Bacterial Vaccine, 371–379 (1982)]. In this case of using human haptoglobin as a ligand, there newly occurs other problem that it is necessary to take a measurement against hepatitis virus. That is, since the human haptoglobin is collected from human blood, it may be contaminated with hepatitis virus and further other unknown infectious factors. This problem is also included in case of using other animal blood. Unfortunately, however, there is no method for surely checking the contamination with hepatitis virus, etc. It is also known that the hepatitis virus etc. can be inactivated by heating it at 60° C. for 10 to 15 hours. It has been found by the present inventors that when haptoglobin is subjected to such a heat treatment, it looses almost the affinity to LPF-HA and hence can not exhibit the desired effect when used in the affinity chromatography.

Moreover, in case of the purification using hydroxyapatite as mentioned above, since the hydroxyapatite is very expensive, this method is not suitable for the purification of LPF-HA in a low cost and on industrial scale, either.

OBJECT OF THE INVENTION

The present inventors have extensively studied on an improved method for the separation and purification of LPF-HA on industrial scale, and have found that the desired highly purified LPF-HA can be obtained very simply and in a very high yield by contacting an LPF-HA-containing solution obtained from culture media of *B. pertussis* with a cellulose sulfate gel, a crosslinked polysaccharide sulfate gel, or a polysaccharide gel chemically bound with dextran sulfate, thereby adsorbing LPF-HA on the gel and separating out any undesirable contaminants, and then eluting LPF-HA from the gel.

Thus, an object of the present invention is to provide a simple and industrial method for the purification of LPF-HA which is biologically active and is useful in a medical field. Another object of the invention is to provide a method for producing a highly purified LPF-HA which is useful for the preparation of *B. pertussis* vaccine. These and other objects and advantages of the present invention will be apparent to skilled persons from the following decription.

SUMMARY OF INVENTION

The method for the purification of LPF-HA of the present invention comprises the steps of treating an LPF-HA-containing solution obtained from culture media of *B. pertussis* with a gel selected from the group consisting of a cellulose sulfate gel, a crosslinked polysaccharide sulfate gel and a polysaccharide gel chemically bound with dextran sulfate, thereby adsorbing LPF-HA on the gel, and then eluting LPF-HA from the gel.

DETAILED DESCRIPTION OF INVENTION

Figure 1:
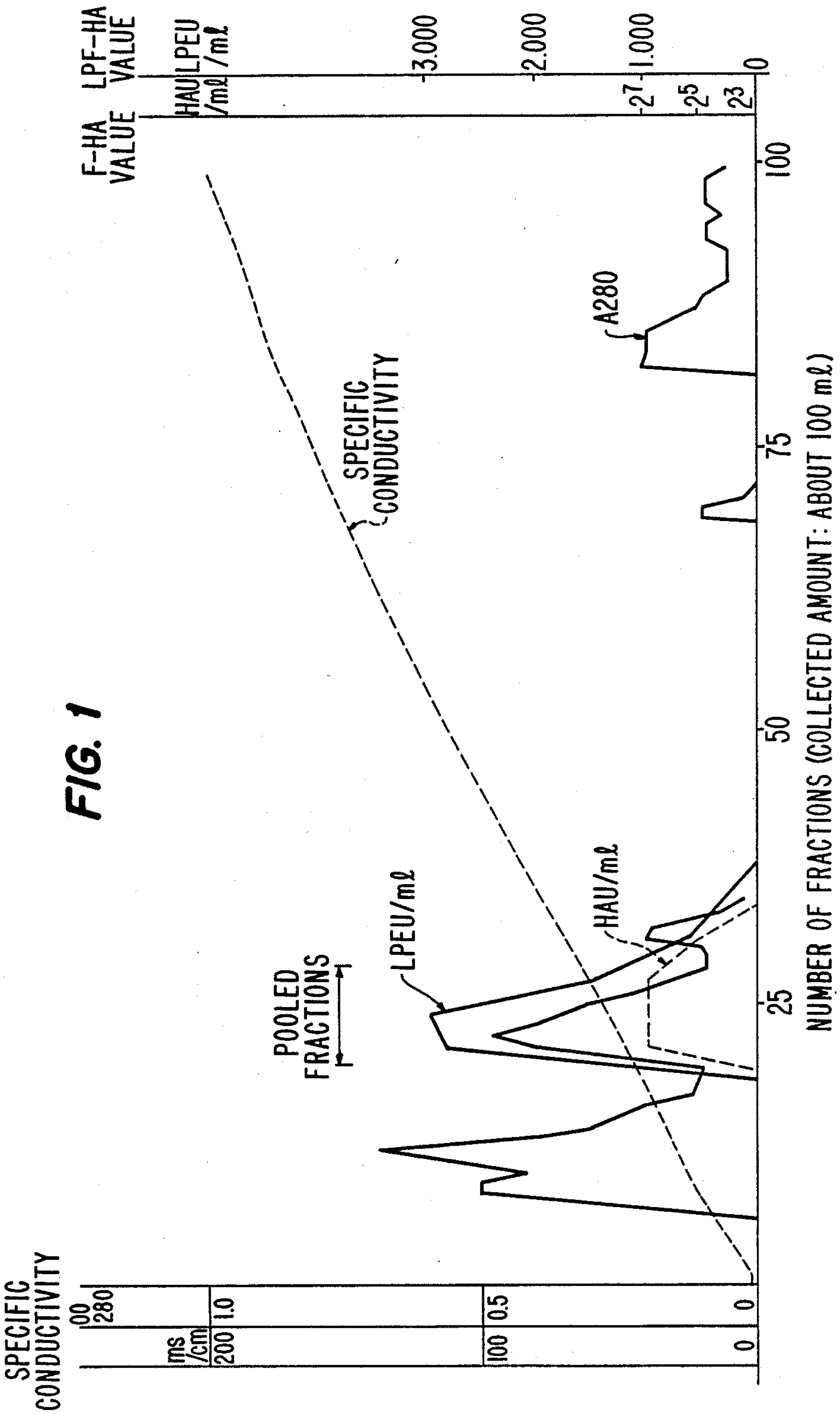

The starting culture media of *B. pertussis* include culture media obtained by culturing *B. pertussis* phase I strain in a conventional liquid medium, such as Cohen-Wheeler medium or Stainer-Scholte medium, in a usual manner, such as stationary culture, shake culture, or spinner culture (this is synonym of shaking culture, aeration culture, and aeration spinner culture). The culture media are used in the present invention after being subjected to centrifugation to remove the cells, or after being fractured, followed by centrifugation, or after being partially purified by conventional purification methods.

The sulfuric acid ester of cellulose used as the cellulose sulfate gel in the present invention is obtained by sulfating a cellulose, preferably a crystalline cellulose or cellulose having crystalline area and non-crystalline area. The sulfuric acid ester of cellulose thus obtained retains well the original shape (preferably spherical shape) of the starting material and is insoluble in an aqueous medium and has excellent physical stability, and hence, is suitable as a gel of chromatography. These starting celluloses are commercially available, for example, Cellulofine GC-15, GH-25, GC-100, or GC-200 (manufactured by Chisso Corp., Japan), and Abicel (manufactured by Asahi Chemical, Japan). The sulfation of the cellulose can be carried out by a conventional method, for example, by treating a gel of cellulose with chlorosulfonic acid, anhydrous sulfuric acid, or other sulfating agent in an organic solvent (e.g. pyridine).

The sulfuric acid ester of a crosslinked polysaccharide includes a sulfuric acid ester of polysaccharides, such as dextran, celluloses, agarose, which is crosslinked with a crosslinking agent, such as epichlorohydrin, dichlorohydrin, dibromohydrin, ethylene glycol bisepoxypropyl ether. The crosslinked polysaccharides are commercially available, for example, crosslinked dextrans such as Sephadex G-10, G-25, G-50, and G-100 (manufactured by Pharmacia, Sweden), crosslinked agaroses such as Sepharose CL-2B, CL-4B, and CL-6B (manufactured by Pharmacia, Sweden), and crosslinked celluloses such as Cellulofine GCL-25, GCL-90 (manufactured by Chisso Corp., Japan). The sulfation of the crosslinked polysaccharide can be carried out by a conventional method, for example, by treating a gel of the crosslinked polysaccharide with chlorosulfonic acid, anhydrous sulfuric acid, or other sulfating agent in an organic solvent (e.g. pyridine).

The polysaccharide gel chemically bound with dextran sulfate is produced by chemically binding a dextran sulfate to a polysaccharide gel derivative. Various products of the dextran sulfate are commercially available, among which the products used usually for biological purposes are preferably used. The polysaccharide gel derivative includes gel derivatives which are prepared by subjecting a polysaccharide (e.g. agarose, dextran, cellulose, etc.) to conventional treatments for giving properties suitable for using as a carrier for chromatography, such as crystallization purification treatment, three-dimensional crosslinking, molding, etc. These products are also commercially available and include, for example, an agarose gel such as Sepharose (manufactured by Pharmacia, Sweden), a dextran gel such as Sephadex (manufactured by Pharmacia, Sweden), a cellulose gel such as Abicel (manufactured by Asahi Chemical, Japan). The chemical binding of the dextran sulfate and the polysaccharide can be done by various methods, for example, by a method of Andersone et al. using cyanobromide (cf. Japanese Patent First Publication No. 114018/1977), or a method using cyanobromide and also lysine (as a spacer) [cf. Bryan M. Turner et al.; Biochimica et Biophysica Acta, 659, 7-14 (1981)]. One product of dextran sulfate-agarose gel is already on the market, for example, dextran sulfate-Sepharose CL4B (manufactured by Pharmacia, Sweden).

The isolation and purification of LPF-HA from a culture of *B. pertussis* with these gels are carried out in the following manner.

The starting LPF-HA-containing solution may be prepared by centrifuging a culture of *B. pertussis*, diluting the supernatant with distilled water or a buffer so as to become a specific conductivity of 0.1 to 5.0 mS/cm, and then subjecting to the adsorption treatment. However, since the supernatant contains usually F-HA (Filamentous hemagglutinin) which has also affinity to the cellulose sulfate gel and other gels, the supernatant may be subjected to chromatography with cellulose sulfate gel or other gels under the conditions that LPF-HA is not adsorbed but F-HA is adsorbed (wherein the starting solution regulated to a specific conductivity of 5.0-25.0 mS/cm and pH 5-9 is passed through a column packed with a cellulose sulfate gel or other gels, which is equilibrated with a buffer of specific conductivity of 5.0-25.0 mS/cm and pH 5-9), and then the fraction passed through the column which does not contain F-HA and contains a large amount of LPF-HA is subjected to the adsorption treatment.

The purification treatment comprising adsorption of LPF-HA onto the cellulose sulfate gel or other gels, washing of the gels adsorbing the LPF-HA and elution of the LPF-HA can be carried out by a conventional industrially employed operation such as batch method or column method. Column method is more advantageous in view of simpler prodecure. In case of column method, the cellulose sulfate gel or other gels are packed in a column, and it is previously equilibrated by passing through an appropriate buffer having a specrfic conductivity of 0.5 to 5.0 mS/cm and a pH of about 5.0 to 9.0, for example a 0.02M McIlvaine's buffer (pH 5.2), and then it is used for the adsorption of LPF-HA.

In the adsorption, the LPF-HA-containing solution is usually regulated to a pH of 5.0 to 9.0 and a specific conductivity of 0.5 to 5.0 mS/cm, and then passed through the column packed with the cellulose sulfate gel or other gel to adsorb LPF-HA. Thereafter, the column is washed with the same buffer as used for the above equilibration, by which contaminated materials are washed out.

The elution of LPF-HA is usually.carried out by passing through an appropriate buffer having a pH of 5.0 to 9.0 and a specific conductivity of 5.0 mS/cm or more, usually 5.0 to 100 mS/cm, preferably by stepwise elution or salt concentration gradient elution. That is, when a diluted supernatant obtained by centrifugation of a culture of *B. pertussis* is used as the starting material, F-HA is also adsorbed together with LPF-HA in the above adsorption condition, and hence, it is necessary to elute LPF-HA under the condition that can elute LPF-HA but not F-HA. It is as follows. Firstly, an appropriate buffer having a pH of 5 to 9 and a spcific conductivity of 5 to 100 mS/cm, preferably 50 to 60 mS/cm (for example, a 0.7M sodium chloride-added 0.02M McIlvaine's buffer) is passed through the column, by which a fraction containing LPF-HA is recovered. Thereafter, a buffer having a specific conductivity of larger than that of the above buffer for elution (e.g. a specific conductivity of 100 to 300 mS/cm) is passed through, by which F-HA and other impurities are eluted out, followed by equilibrating the cellulose sulfate gel or other gel in order to re-use the gel.

The most preferable elution is carried out by a salt concentration gradient elution method. In case of using an LPF-HA-containing solution, from which F-HA is previously removed, the elution is carried out by using a buffer having such a salt concentration gradient as a specific conductivity of 0.5→300 mS/cm (for example, a 0.02M McIlvaine's buffer (pH 5.2) having a sodium chloride concentration gradient of 0→4.0M) to obtain an LPF-HA-containing fraction, by which a highly purified LPF-HA can be obtained.

According to the purification method of the present invention, the purification degree of LPF-HA becomes several ten folds and further the recovery rate of LPF-HA reaches to from more than 90% to almost 100%. Beside, the purified LPF-HA has so high specific activity as 0.8–0.9$\times 10^5$ LPF-Hp-ELISA unit/mg protein, and further, forms a single band in a polyacrylamide disc electrophoresis analysis (pH 4.5), which means that *B. pertussis* endotoxin is almost completely removed.

Thus, according to the above purification method, the desired LPF-HA can be isolated from the starting culture of *B. pertussis* in a high yield and high purity with very simple operation, and the chromatography adsorbent can be prepared in a low cost and also can be used repeatedly without deterioration, and hence the method is excellent from economical viewpoint. Accordingly, the purification method of the present invention is very excellent as an industrial method for production of a highly purified LPF-HA. If necessary, the purification may be combined with conventional purification methods, such as sucrose density gradient ultracentrifugation, ion exchange chromatography, etc., by which a more excellent product can be obtained.

The purified LPF-HA obtained by the present invention is very pure and does not contain other proteins, lipids, saccharides, etc., and further, endotoxin is almost completely removed, and hence, it can be used as various reagents utilizing the biological activity, for the preparation of medicaments and also for the preparation of *B. pertussis* vaccine.

EXAMPLES

The present invention is illustrated by the following Preparations and Examples, but should not be construed to be limited thereto.

PREPARATION 1

To pyridine (600 ml) is added dropwise chlorosulfonic acid (117 g) at below 0° C. After the addition, the mixture is heated to 65°–70° C. To the mixture is added crystalline cellulose gel (Cellulofine GC-15, manufactured by Chisso Corp.) (80 g), and the mixture is stirred at 65°–70° C. for 3 hours. After the reaction, the reaction mixture is cooled and neutralized with 10% aqueous sodium hydroxide. The gel thus obtained is separated by filtration and washed well with 0.01M phosphate buffer-aqueous sodium chloride mixture to give a cellulose sulfate gel.

PREPARATION 2

To pyridine (600 ml) is added dropwise chlorosulfonic acid (117 g) at below 0° C. After the addition, the mixture is heated to 65°–70° C. To the mixture is added crystalline cellulose (Abicel for chromatography, manufactured by Asahi Chemical, Japan) (80 g), and the mixture is stirred at 65°–70° C. for 4 hours. After the reaction, the reaction mixture is cooled and then neutralized with 10% aqueous sodium hydroxide. The gel thus obtained is separated by filtration and washed well with 0.01M phosphate buffer-aqueous sodium chloride mixture to give a cellulose sulfate gel.

PREPARATION 3

To pyridine (200 ml) is added dropwise chlorosulfonic acid (11 ml) at below 0° C. After the addition, the mixture is heated to 65°–70° C. To the mixture is added epichlorohydrin-crosslinked dextran (Sephadex G-50, manufactured by Pharmacia, Sweden) (7.5 g), and the mixture is stirred at 65°–70° C. for 4 hours. After the reaction, the reaction mixture is cooled and then neutralized with aqueous sodium hydroxide. The gel thus obtained is separated by filtration and washed well with 0.01M phosphate buffered saline solution to give a crosslinked dextran sulfate.

PREPARATION 4

To a mixture (210 ml) of pyridine and chlorosulfonic acid prepared in the same manner as described in Preparation 3 is added crosslinked cellulose (Cellulofine GCL-25, manufactured by Chisso Corp., Japan) (7.5 g), and the mixture is stirred at 65°–70° C. for 4 hours. After the reaction, the reaction mixture is cooled and then neutralized with aqueous sodium hydroxide. The gel thus obtained is separated by filtration and washed well with 0.01M phosphate buffered saline solution to give a crosslinked cellulose sulfate (7.2 g).

PREPARATION 5

To a mixture (210 ml) of pyridine and chlorosulfonic acid prepared in the same manner as described in Preparation 3 is added 30 ml of crosslinked agarose (Sepharose CL-6B, manufactured by Pharmacia, Sweden) containing pyridine, and the mixture is stirred at 65°–70° C. for 4 hours. After the reaction, the reaction mixture is cooled and then neutralized with aqueous sodium hydroxide. The gel thus obtained is separated by filtration and washed well with 0.01M phosphate buffered saline solution to give a crosslinked agarose sulfate (23 ml).

PREPARATION 6

Sodium dextran sulfate (5 g) is dissolved in 0.5M aqueous sodium carbonate (200 ml), and thereto is added Sepharose CL-4B (agarose gel, manufactured by Pharmacia, Sweden) (20 ml) which is equilibrated by 0.5M aqueous sodium carbonate, and the mixture is gently stirred. To the mixture is added with stirring a solution of cyano bromide (10 g) in distilled water (100 ml). The mixture is maintained for 15 minutes while keeping at pH 11 by adding 5M aqueous sodium hydroxide. Thereafter, the mixture is stirred at room temperature for 17 hours, while allowing to lower the pH value. After the reaction, the reaction mixture is filtered with a glass filter, and the gel thus obtained is washed well with 0.15M sodium chloride-added phosphate buffer (pH 7.2) to give dextran sulfate agarose gel (20 ml).

EXAMPLE 1

The Cellulofine GC-15 sulfate gel obtained in the same manner as described in the above Preparation 1 is packed within a column (40 mmϕ×200 mm), and therethrough is passed distilled water (1.0 liter). A supernatant (500 ml) of a fermenter culture of *B. pertussis* phase I Tohama strain is diluted with distilled water in 10 folds and the diluted solution (specific conductivity: about 1.5 mS/cm) is passed through the column. After washing well the column with 0.02M McIlvaine's buffer (pH 5.2, about 500 ml), the adsorbed material is eluted with 0.02M sodium chloride-added McIlvaine's buffer (specific conductivity: about 2.0 mS/cm, pH 5.2, 2,000 ml) in the concentration gradient of sodium chloride of 0→4.0M, whereby fractions (each about 20 ml) are collected and then the fraction containing LPF-HA (about 130 ml) is pooled.

The analitical data and experimental data of the starting material and the purified LPF-HA fraction are shown

TABLE 1

| Analytical items | Samples: Supernatant of culture (starting material) | Samples: Fraction of purified LPF-HA |
|---|---|---|
| Amount of sample (ml) | 500 | 130 |
| Content of LPF-HA (1) (LPEU/ml) | 500 | 1,750 |
| Content of protein (2) (mg/ml) | 0.250 | 0.020 |
| Specific activity of LPF-HA (LPEU/mg protein) | $2 \times 10^3$ | $8.8 \times 10^4$ |
| Recovery rate of LPF-HA (%) | (100) | 84 |
| Pyrogen test in rabbit (Total in three rabbits, °C.) (3) | 4.5 | 0.9 |

[Notes]: (1) It shows LPF-HA unit which was measured by in vitro test: Hapto-ELISA method (cf. Sato, et al, Symposium on Toxins, Proceeding of the 28th Symposium on Toxins, 141-144 (1981)
(2) It is shown as a protein content when calculated as protein nitrogen measured by Kjeldahl method × 6.25.
(5) It was done in accordance with the method described in Minimum Reguirement of Biological Products, Ministry of Health and Welfare, Japan, #287, 1981, wherein the test sample was diluted until protein content of 6.25 μg/ml.

EXAMPLE 2

Cellulose sulfate gel obtained in the same manner as described in the above Preparation 1 (each 1 liter) is packed within two columns (80 mmϕ×200 mm). One column is equilibrated by passing through a 0.2M sodium-added 0.01M phosphate butter (pH 7.2, specific conductivity: 21.0 mS/cm), and as to other column distilled water is passed through.

A supernatant (20.0 liters) of a fermenter culture of *B. pertussis* phase I Tohama strain is passed through the above column which is equilibrated by phosphate buffer. The fraction passed through the column is pooled. Besides, the column is washed with 0.2M sodium chloride-added 0.01M phosphate buffer (specific conductivity: 21.0 mS/cm), and the fraction (21.0 liters) of washing liquid which contains LPF-HA is also pooled together with the above passed through fraction. The pooled fractions are diluted with distilled water to regulate the specific conductivity to about 1.5 mS/cm) and are passed through the column passed through by distilled as above water. After washing well the column with 0.02M McIlvaine's buffer (specific conductivity: 2.0 mS/cm, pH 5.2, about 20 liters), the adsorbed material is eluted with 0.02M McIlvaine's buffer (pH 5.2, 10 liters) in the concentration gradient of sodium chloride of 0→4.0M, whereby fractions (1.1 liter) containing LPF-HA are collected.

The analitical data and experimental data of the starting material and the purified LPF-HA fraction are shown in Table 2.

Besides, the chromatogram of the eluted solution from the LPF-HA-adsorbed cellulose sulfate gel is shown in the accompanying FIG. 1. In FIG. 1, the abscissa axis means number of fractions (amount: about 100 ml), and the ordinate axis means an absorption value at a wave length of 280 nm ($A_{280}$) and a specific conductivity (mS/cm) of the fraction, an LPF-HA content (LPEU/ml) of the fraction which is measured by hapto-ELISA method and an HA value (HAU/ml) of the fraction which is measured by an agglutination test in chicken. [cf. Sato, Y. et al., Infect. Immun., 7, 929 (1973)]

TABLE 2

| Analytical items | Samples: Supernatant of culture (starting material) | Samples: Fraction of purified LPF-HA |
|---|---|---|
| Amount of sample (ml) | 20,000 | 1,100 |
| Content of LPF-HA (1) (LPEU/ml) | 1,000 | 16,500 |
| Content of protein (2) (mg/ml) | 0.360 | 0.180 |
| Specific activity of LPF-HA (LPEU/mg protein) | $2.8 \times 10^3$ | $9.2 \times 10^4$ |
| Recovery rate of LPF-HA (%) | (100) | 90 |
| Pyrogen test in rabbit (Total in three rabbits, °C.) (3) | 5.3 | 1.1 |

[Notes]: The notes in (1), (2) and (3) are the same as in the above Table 1.

EXAMPLE 3

The crosslinked cellulose sulfate gel (5 ml) obtained in the same manner as described in the above Preparation 4 is packed within a column (40 mmϕ×200 mm), and therethrough is passed distilled water (200 ml). A supernatant (100 ml) of a fermenter culture of *B. pertussis* phase I Tohama strain is diluted with distilled water in 7 folds and the diluted solution (specific conductivity: about 3.0 mS/cm) is passed through the column. After washing well the column with 0.02M McIlvaine's buffer (pH 5.2, about 200 ml), the absorbed material is eluted with 0.02M sodium chloride-added McIlvaine's buffer (specific conductivity: about 2.0 mS/cm, pH 5.2, 50 ml) in the concentration gradient of sodium chloride of 0→4.0M, whereby fractions (each about 1 ml) are collected and then the fraction containing LPF-HA (about 6 ml) is pooled.

The analytical data and experimental data of the starting material and the purified LPF-HA fraction are shown in Table 3.

TABLE 3

| Analytical items | Samples: Supernatant of culture (starting material) | Samples: Fraction of purified LPF-HA |
|---|---|---|
| Amount of sample (ml) | 100 | 6 |
| Content of LPF-HA (1) (LPEU/ml) | 500 | 6,400 |
| Content of protein (2) (mg/ml) | 0.250 | 0.073 |
| Specific activity of LPF-HA | $2 \times 10^3$ | $8.8 \times 10^4$ |

TABLE 3-continued

| Analytical items | Samples: Supernatant of culture (starting material) | Fraction of purified LPF-HA |
|---|---|---|
| (LPEU/mg protein) | | |
| Recovery rate of LPF-HA (%) | (100) | 77 |
| Pyrogen test in rabbit (Total in three rabbits, °C.) (3) | 4.7 | 0.9 |

[Notes]: The notes in (1), (2) and (3) are the same as in Table. 1.

EXAMPLE 4

The dextran sulfate agarose gel (5 ml) obtained in the same manner as described in the above Preparation 6 is packed within a column (40 mmφ×200 mm), and therethrough is passed distilled water (100 ml). A supernatant (100 ml) of a fermenter culture of *B. pertussis* phase I Tohama strain is diluted with distilled water in 8 folds and the diluted solution (specific conductivity: about 3.0 mS/cm) is passed through the column. After washing well the column with 0.02M McIlvaine's buffer (pH 5.2, about 300 ml), the adsorbed material is eluted with 0.02M sodium chloride-added McIlvaine's buffer (pH 5.2, 100 ml) in the concentration gradient of sodium chloride of 0→4.0M, whereby fractions (each about 2 ml) are collected and then the fraction containing LPF-HA (about 12 ml) is pooled.

The analytical data and experimental data of the starting material and the purified LPF-HA fraction are shown in Table 4.

TABLE 4

| Analytical items | Samples: Supernatant of culture (starting material) | Fraction of purified LPF-HA |
|---|---|---|
| Amount of sample (ml) | 100 | 12 |
| Content of LPF-HA (1) (LPEU/ml) | 500 | 3,750 |
| Content of protein (2) (mg/ml) | 0.250 | 0.042 |
| Specific activity of LPF-HA (LPEU/mg protein) | $2 \times 10^3$ | $8.8 \times 10^4$ |
| Recovery rate of LPF-HA (%) | (100) | 90 |
| Pyrogen test in rabbit (Total in three rabbits, | 4.7 | 0.9 |

TABLE 4-continued

| Analytical items | Samples: Supernatant of culture (starting material) | Fraction of purified LPF-HA |
|---|---|---|
| °C.) (3) | | |

[Notes]: The notes in (1), (2) and (3) are the same as in Table 1.

What is claimed is:

1. A method for the purification of LPF-HA (Leucocytosis promoting factor hemagglutinin) produced by *Bordetella pertussis,* which comprises centrifuging a culture of *B. pertussis,* regulating the supernatant to a specific conducitivity of 5.0 to 25.0 mS/cm and a pH of 5 to 9, passing the regulated supernatant through a column packed with a gel selected from the group consisting of a cellulose sulfate gel and a crosslinked polysaccharide sulfate gel which has been previously equilibrated by treatment with a buffer having a pH of 5.0 to 9.0 and a specific conductivity of 0.5 to 5.0 mS/cm, subjecting the resulting LPF-HA-containing solution to absorption of the LPF-HA with said gel under the conditions of pH of 5.0 to 9.0, a temperature of 0° to 30° C. and a specific conductivity of 0.5 to 5.0 mS/cm, and eluting the absorbed LPF-HA from the gel with a buffer having a specific conductivity of 5.0 to 100.0 mS/cm, said cellulose gel and said crosslinked polysaccharide sulfate gel being prepared by sulfating cellulose and a crosslinked polysaccharide, respectively, with a sulfating agent in an organic solvent.

2. The method according to claim 1, wherein the gel is selected from the group consisting of a dextran sulfate-agarose gel, a dextran sulfate-dextran gel, and a dextran sulfate-cellulose gel.

3. The method according to claim 1, wherein the LPF-HA-adsorbed gel is washed with a buffer having a specific conductivity of 0.5 to 5.0 mS/cm before the elution.

4. The method according to claim 1, wherein the cellulose sulfate is a sulfuric acid ester of a cellulose selected from a crystalline cellulose and a cellulose having crystalline area and non-crystalline area.

5. The method according to claim 1, wherein the crosslinked polysaccharide sulfate is a member selected from the group consisting of a crosslinked cellulose sulfate and a crosslinked dextran sulfate.

6. The method according to claim 5, wherein the crosslinked cellulose sulfate is an epichlorohydrin-crosslinked cellulose sulfate.

7. The method according to claim 5, wherein the crosslinked dextran sulfate is an epichlorohydrin-crosslinked dextran sulfate.

* * * * *